United States Patent [19]

Lawrence et al.

[11] Patent Number: 5,705,698
[45] Date of Patent: Jan. 6, 1998

[54] PROCESS FOR THE PRODUCTION OF PENDIMETHALIN AND ISO-PENDIMETHALIN

[75] Inventors: Lowell J. Lawrence; Stefan Kwiatkowski; Krzysztof Pupek; Miroslaw J. Golinski, all of Richmond, Ky.

[73] Assignee: SRM Chemical, Ltd. Co., League City, Tex.

[21] Appl. No.: 621,403

[22] Filed: Mar. 25, 1996

[51] Int. Cl.$^6$ .................................. C07C 209/22
[52] U.S. Cl. ........................................ 564/419
[58] Field of Search .................................. 564/419

[56] References Cited

U.S. PATENT DOCUMENTS 4,609,759  9/1986  Carr ........................ 564/395

Primary Examiner—Richard L. Raymond
Attorney, Agent, or Firm—King & Schickli

[57] ABSTRACT

A process is provided for the preparation of isometrically pure pendimethalin and iso-pendimethalin as well as mixtures thereof.

2 Claims, No Drawings

PROCESS FOR THE PRODUCTION OF PENDIMETHALIN AND ISO-PENDIMETHALIN

TECHNICAL FIELD

This application claims the benefit under 35 USC § 119 (e) of U.S. provisional application Ser. No. 60/011,936, filed Feb. 20, 1996, entitled "Process for the Production of N-Alkyl-Dinitroalkylanilines".

The present invention relates generally to an improved process for the production of pendimethalin and iso-pendimethalin in a cost effective, efficient and environmentally friendly manner.

BACKGROUND OF THE INVENTION

N-alkyl-dinitro-o-dialkylanilines such as N-(1-ethylpropyl)-3,4-dimethyl-2,6 dinitroaniline [N-(1-ethylpropyl)-3,4-dimethyl-2,6-dinitrobenzenamine; pendimethalin] are known selective herbicides generally used for pre-emergence control of annual broad-leaved weeds and grasses in cotton, soybeans, rice, barley, beans, alliums, vines, ornamentals and orchards of fruit and nut trees. They are also used to control suckers of tobacco.

One process for the synthesis of pendimethalin is generally described in U.S. Pat. No. 4,609,759 to Carr. This process starts with a two step nitration of o-xylene to a mixture of 1,2,6-trinitro-o-xylene and 1,4,6-trinitro-o-xylene. This mixture is then treated with 1-ethylpropylamine to afford N-(1-ethylpropyl)-3,4-dimethyl-2,6 dinitroaniline. It is stated in this patent that only the 1-nitro group of 1,2,6-trinitro-o-xylene is labile to nucleophilic aromatic substitution and that the 1,4,6-trinitro-o-xylene remains unreacted. The N-(1-ethylpropyl)-3,4-dimethyl-2,6-dinitroaniline product is separated from the "unreacted" 1,4,6-trinitro-o-xylene by contacting the reaction product with concentrated sulfuric acid. The resulting salt dissolves in the aqueous phase and is separated from the unreacted organic phase which remains water insoluble.

Contrary to the explicit teachings of the Carr patent, we have now found that the 1-nitro group of the 1,4,6-trinitro-o-xylene co-intermediate is in fact also labile to nucleophilic aromatic substitution and does in fact react in similar fashion with 1-ethylpropylamine so that reaction of the latter with a mixture of 1,2,6-trinitro-o-xylene and 1,4,6-trinitro-o-xylene creates a mixture of isomeric N-alkyl aniline derivatives. Further, the proposed sulfuric acid separation treatment set forth in the Carr patent is completely ineffective in separating these isomers.

From the above description it should be appreciated that a need exists for an improved process for producing isometrically pure pendimethalin and even previously unrecognized iso-pendimethalin in a more economical and environmentally safe manner.

SUMMARY OF THE INVENTION

Accordingly, it is a primary object of the present invention to provide a process for the production of N-alkyl-dinitro-o-dialkylanilines including, for example, pendimethalin and iso-pendimethalin overcoming the above-identified limitations and disadvantages of the prior art.

Another object of the invention is to provide a process for the production of pendimethalin/iso-pendimethalin from readily available and relatively inexpensive starting materials and relatively safe and inexpensive reagents whereby the environmentally safe and economical production of thereof results.

Other objects and advantages of the present invention will become apparent as the description hereof proceeds.

In satisfaction of the foregoing objects and advantages there is provided by this invention a process for producing pendimethalin/iso-pendimethalin. The process generally comprises the nitrating of a readily available starting material, o-xylene, with the general chemical formula:

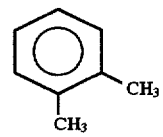

in order to obtain a mixture of the following two trinitro substituted intermediates having the general chemical formulae:

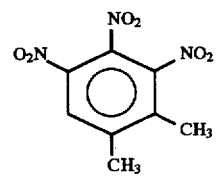   I

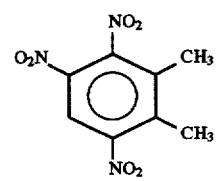   II

Compound I may be separated from compound II by means described herein or any other procedure known in the art that is effective for the purpose of such a separation.

Next, the purified trinitro substituted intermediate is subjected to amination by reacting with 1-ethylpropylamine. In the case of compound I this simple process produces the compound shown in formula III, pendimethalin. In the case of compound II, this process produces the hitherto undescribed compound shown in formula IV, "iso-pendimethalin". Alternatively, the mixture of compounds I and II can be reacted directly with a primary or secondary amine to produce a mixture of the compounds III and IV, pendimethalin and iso-pendimethalin.

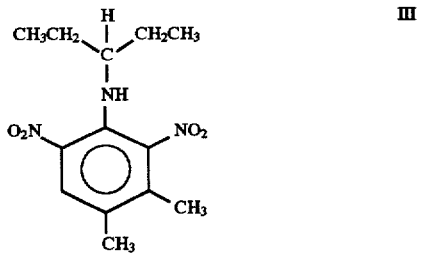   III

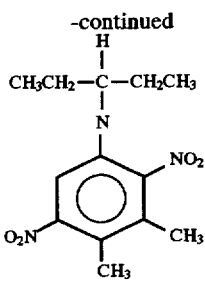

DETAILED DESCRIPTION OF THE INVENTION

As indicated above, the present invention relates to a process for producing pure N-alkyl-dinitro-o-dialkylanilines, pendimethalin and iso-pendimethalin. Such products are useful as selected herbicides used for pre-emergence control of annual broad-weeds and grasses in, for example, cotton, soybean, rice, barley, beans, alliums, vines, ornamentals and orchids of fruit and nut trees. They may also be useful as intermediates for preparation of other herbicides.

The improved process for producing pure N-alkyl-dinitro-o-dialkylanilines comprises three relatively simple steps.

The first is the nitrating of a readily available aromatic starting material, o-xylene, having a chemical formula

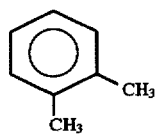

in order to obtain a mixture of trinitro intermediates having the general chemical formulae:

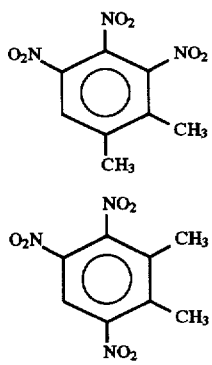

Of course, during the nitration step, small quantities of other nitrogen substituted compounds are produced. Accordingly, the second step in the method is the separating of the desired trinitro substituted intermediate of the chemical formula shown above from these other nitro-substituted products. The undesired and now separated products may then be recycled to the nitration step in order to minimize waste and improve the economic implementation of the present process.

The third and final step is the amination of the desired trinitro substituted intermediate using 1-ethylpropylamine.

More specifically describing the invention, the first step of the improved process for synthesizing isometrically pure pendimethalin/iso-pendimethalin includes preparation of the nitration mixture preferably comprising approximately 2.5 parts of concentrated nitric acid and approximately 9.0 parts of concentrated sulfuric acid. To this nitration mixture is added approximately one part of the readily available aromatic starting material o-xylene having the chemical formula [1] as described above. Throughout the addition the mixture is stirred and external cooling such as by means of an ice bath is provided. When the addition of the o-xylene starting material is completed, stirring is continued until the reaction temperature increases to ambient temperature.

Next, an additional amount of approximately 1part of concentrated nitric acid is added while stirring continues. As a result, the temperature of the reaction mixture is gradually increased to approximately 100° C. within about 2.5 hours and it is then maintained at substantially 100° C for about 30 minutes. Stirring continues as the reaction mixture is then cooled to room temperature in order to initiate precipitation of the desired trinitro intermediate of the chemical formula [2] noted above. Cooling is continued to 1° C. in order to complete the precipitation of the desired trinitro substituted intermediate which is filtered off from the mixture and washed with 150 parts of water. The trinitro substituted intermediate is then vacuum dried to afford a clean product.

Next, the desired trinitro substituted intermediate is separated from other nitrated products by pouring 1 part of the filtrate into approximately 10 parts of ice and filtering off the precipitate. After that the precipitate is washed with water to a pH of approximately 6 and crystallized from approximately 12 parts of isopropyl alcohol. This affords a relatively pure intermediate (i.e. greater than 95% purity) at high yield (i.e. greater than 80% yield). The solvent may then be evaporated from the remaining filtrate in order to recover a mixture of dinitro and other undesired trinitro substituted compounds that may be recycled in the next nitration bath in order to reduce processing costs and eliminate waste.

Next is the aminating of the desired trinitro substituted intermediate recovered in the preceding separation step. Specifically, 1 part of the pure trinitro substituted intermediate is dissolved in two parts of methyl alcohol. Advantageously methyl alcohol is readily available at a reasonable price and it is more environmentally friendly than the aromatic and halogenated solvents employed in prior art procedures. Of course, other alcohols such as ethyl alcohol could be utilized if desired.

Next is the amination step. Preferably, 1.1 parts of 1-ethylpropylamine are added while stirring. The mixture is then warmed to 45°–50° C. within about 15 minutes. In order to complete amination, the reaction is then stirred at 50° C. for an additional 45 minutes followed by cooling in icy water and filtering under suction. An additional quantity of the desired product may be generated by concentrating the filtrate to $\frac{1}{10}$ of the primary volume and filtering the crystals that are produced.

By following this process of the present invention as just described, one may obtain high purity pendimethalin.

Of course, it should also be appreciated that it is possible to prepare pure iso-pendimethalin if desired. Specifically, the previously "undesired" trinitro substituted by-product compounds recovered during the separation step may be dissolved in two parts of methyl alcohol. Then 1.1 parts of 1-ethylpropylamine is added to this solution at ambient temperature with stirring. The stirring continues as the mixture is heated to 50° C. and maintained at that temperature for 4.5 hours in order to complete the amination step. After this time, the mixture is cooled in icy water and a crystalline precipitate is filtered off and dried under suction. By following the present process, it should therefore be appreciated that one may obtain high purity iso-pendimethalin which also shows promising herbicidal activity as a preemergent herbicide.

As also noted above, the "undesired" nitrating step by-products may be recycled. Specifically, the separated "undesired" filtrate is slowly added to the icy water while being stirred and cooled to below 5° C. The resulting precipitated mixture is then filtered off and the cake is washed with water until approximately pH 6 is obtained. The filtrate is then air dried.

Next, the crystals are dissolved in 10 parts of dimethyl-sulfoxide and reduced to a mixture of dinitro substituted compounds by the addition of 1.2 parts of sodium borohydride with stirring at ambient temperature for a period of approximately 40 minutes. After this time the reaction mixture is poured into approximately 40 parts of water containing about two parts of concentrated sulfuric acid and then extracted with two approximately 20 part portions of hexane. From the collected extracts the solvent may be evaporated and a thick residue of dinitro compounds is obtained. This dinitro compound residue is then recycled into the next nitration bath.

EXAMPLE 1

Reaction 1

Nitration of O-xylene and Preparation of Trinitro-o-xylene Derivative

A stirred and cooled to −10° C. solution of fuming (30% $SO_3$) sulfuric acid (48.8 ml) as available from ALDRICH, of Milwaukee, Wis. and 95.5% fuming nitric acid (20.7 ml) as available from FLUKA, of Ronkionkioha, N.Y. was placed in a 250 ml round bottom three neck flask that is placed in a cooling/heating bath and equipped with a thermometer, a stirrer and a dropping funnel. To this solution was added 21.23 g (24.4 ml) of 98% pure o-xylene as available from ALDRICH, of Milwaukee, Wis. drop wise over a period of 25 minutes. The temperature was maintained below −3° C. during addition of the first 6 ml of o-xylene, and below +5° C. during the addition of the next 6 ml of o-xylene and finally below +10° C. addition of the rest of o-xylene. After being stirred for 5 minutes more an additional volume of 34.5 ml of fuming sulfuric acid was added with stirring in three equal portions while maintaining the temperature below 24° C. This was followed by the addition of 8.3 ml of fuming nitric acid. After the next 30 minutes of stirring the reaction mixture at 40° C., one more portion of 8.3 ml of fuming nitric acid was added and the temperature was increased to 65° C. Then the stirring was continued for 30 minutes while the temperature was increased up to 85° C. at which it was maintained for the next 2 hours. After this time, the contents of the reactor was cooled to 18° C. within 4 hours causing precipitation of the desired 1,2,6-trinitro-o-xylene that was filtered off under suction. The cake was then well pressed and washed with equal volume portions (i.e. ~50 ml) of 96% sulfuric acid then with water until the filtrate of the pH reached 6.0. This afforded after vacuum drying 8.74 g (18.1% yield) of more than 98% pure product with the melting point of 115° C. (as given for 1,2,6-trinitro-o-xylene by Crossly et al.; *Journal of Chem. Society,* 1909, p. 204).

Reaction 2

Preparation of 3,4-dimethyl-2,6-dinitro-N-(ethylpropyl) aniline, Pendimethalin In a 100 ml three necked round bottomed flask equipped with a reflux condenser, thermometer and dropping funnel, the 8.74 g of the 1,2,6-trinitro-o-xylene from reaction 1 were suspended in 15 ml of methyl alcohol as available from FISHER, Atlanta, Ga. Additionally, 6.95 g (9.3 ml) of 1-ethylpropylamine as available from ALDRICH, Milwaukee, Wis. were added dropwise into the solution with magnetic stirring. An increase of the temperature from ambient to +40° C. was observed during the 15 minutes of addition time. As the mixture became intensely orange colored it was stirred and boiled under the reflux condenser for 2 hours and 45 minutes until evolution of nitrogen ceased and the trinitro substrate was fully consumed. Afterwards, the reaction mixture was cooled with an ice-water bath to afford crystallization of the product which was then filtered off and air dried yielding 8.22 g (91% yield) of more than 99% pure pendimethalin in the form of orange crystals with the melting point 56°–57° C. as given in the Merck Index for the same compound. NMR data was also collected utilizing a 300 MHz instrument as manufactured by Varian of Palo Alto, Calif. That data included: [$^1$H] NMR 300 MHz, 0.5% solution in $CDCl_3$, δ ppm; 0.88t, J=7.57 Hz, 6 H; 1.50m, 4H; 2.18s, 3H; 2.26s, 3H; 3.15m, 1H; 7.62sbr, 1H; 8.07s, 1H.

EXAMPLE 2

Separation of 1,4,6-Trinitro-O-Xylene

The first filtrate from the separation of 1,2,6-trinitro-o-xylene was extracted three times with 80 ml portions of methylene chloride. The extracts were combined and the volatiles were evaporated to yield an oily mixture of 3,5-dinitro-o-xylene with both of the trinitro-o-xylene isomers. This oil was crystallized from 12 parts of isopropyl alcohol to afford 27.4 g (91.7% yield) of pure 1,4,6-trinitro-o-xylene having a melting point of 72° C. as given by Crossly et al.

Reaction 1

Preparation of 2,3-dimethyl-4,6-dinitro-N-(1-ethylpropyl) aniline, Iso-pendimethalin The reaction of 1,4,6-trinitro-o-xylene with 1-ethylpropylamine was performed exactly as in Example 1, Reaction 2 with the exception of heating time that was extended to 4.5 hours.

The reaction yielded 8.4 g of 99% pure orange crystals of iso-pendimethalin with 94% yield and with the melting point of 75°–76° C. The molecular weight was confirmed to be 249 mu by measuring its mass spectrum utilizing a HP 5989B mass spectrometer as manufactured by Hewlett-Packard of Avondale, Pa. The NMR spectrum data gathered utilizing a 300 MHz NMR as manufactured by Varian of Palo Alto, Calif. confirms that the product has an isomeric structure to that of pendimethalin. The results include: [$^1$H] NMR 300 MHz, 0.5% solution in $CDCl_3$δ ppm; 0.90t, J=7.32 Hz, 6H; 1.54m, 4H; 2.34s, 3H; 2.51s, 3H; 3.44m, 1H; 7.35sbr, 1H; 8.66s, 1H.

EXAMPLE 3

Preparation of Isomeric Mixture of Pendimethalin and Iso-Pendimethalin

The post reaction mixture from Example 1, Reaction 1, was poured with stirring into 5 parts volume of icy-water. The separated precipitate was filtered off and washed on a filter with water until the pH of the filtrate reacted 6.0. Then, after air drying, the mixture was suspended in 150 ml of methyl alcohol and 35 g of 1-ethylpropylamine (46.7 ml) were added. Stirring and boiling of the reaction mixture were maintained for 6 hours. Then the solution was cooled to ambient temperature. Precipitating orange crystals were filtered off and washed once with 45 ml of icy cold methyl alcohol, then vacuumed dried to afford a mixture of pendimethalin/iso-pendimethalin (approximate ration 1:3) in amount of 44.8 g (90% yield).

EXAMPLE 4

Recycling of Undesired Nitration Products

The oily residue from the methylene chloride extraction from Example 2 was dissolved in 200 ml of pure dimethylsulfoxide as available from ALDRICH of Milwaukee, Wis. into this solution with external cooling and efficient heating, sodium borohydride (2.4 g) was added in small portions over the period of 20 minutes. Then the solution was poured into 500 ml of 5% sulfuric acid and extracted three times with 150 ml of hexane. The hexane extracts were combined and the volatiles were evaporated yielding an oily residue that was crystallized from 250 ml of ethyl alcohol to afford 21.4 g (65% yield) of 3.5-dinitro-o-xylene having a melting point of 75°–76° C. identical with the product described by Crossly et al. This product may be recycled in the nitration bath.

In summary, numerous benefits have been described which result from employing the concepts of the present. A more economical process is provided for the production of isometrically pure pendimethalin. Further, a process for the production of isometrically pure iso-pendimethalin is provided for the first time. Of course, if the separation step is not performed, it is possible to prepare a mixture of pendimethalin and iso-pendimethalin if this is desired. Advantageously, the process is environmentally sound avoiding the use of aromatic or halogenated solvents and reagents. Further, all by-products formed may be utilized and recycled in the earlier steps of the process. In this description, reference has been made to certain preferred procedures. It should be appreciated, however, as obvious modifications or variations thereof become apparent to those skilled in the art, this invention is not to be considered as limited thereto.

We claim:

1. A process for producing isometrically pure pendimethalin comprising:

nitrating an o-xylene starting material in order to produce trinitro substituted intermediates I and II having chemical formula:

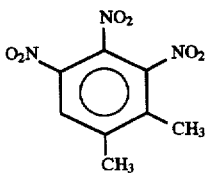

(I)

and

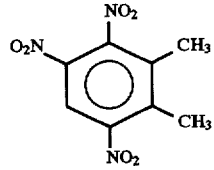

(II)

separating trinitro substituted intermediate (I) from trinitro substituted intermediate (II); and aminating said separated trinitro substituted intermediate (I) with 1-ethylpropylamine to produce pendimethalin.

2. A process for producing isometrically pure iso-pendimethalin, comprising:

nitrating an o-xylene starting material in order to produce trinitro substituted intermediates I and II having chemical formula:

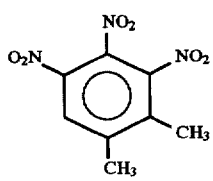

(I)

and

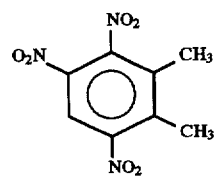

(II)

separating trinitro substituted intermediate (II) from trinitro substituted intermediate (I); and aminating said separated trinitro substituted intermediate (II) with 1-ethylpropylamine to produce iso-pendimethalin.

* * * * *

UNITED STATES PATENT AND TRADEMARK OFFICE
CERTIFICATE OF CORRECTION

PATENT NO. : 5,705,698

DATED : January 6, 1998

INVENTOR(S) : Lowell J. Lawrence et al.

It is certified that error appears in the above-identified patent and that said Letters Patent is hereby corrected as shown below:

In the Abstract, line 1, change "isometrically" to --isomerically--.

In Column 1, lines 28, 32, 45, change "1,2,6" to --3,4,5--.

In Column 1, lines 28, 33, 36, 41 and 45, change "1,4,6" to --3,4,6--.

In Column 1, line 31, change "1-nitro" to --4-nitro--.

In Column 1, line 41, change "1-nitro" to --3-nitro--.

In Column 1, line 52, change "metrically" to --merically--.

In Column 1, line 53 following "iso-pendimethalin" insert --(N-[1-ethylpropyl]-2,3-dimethyl-4,6-dinitroaniline)--. In Column 1, line 66, delete "of".

In Column 2, lines 53-54, change "a primary or secondary amine" to --1-ethylpropylamine--.

In Column 3, change formula IV to read as follows:

UNITED STATES PATENT AND TRADEMARK OFFICE
CERTIFICATE OF CORRECTION

PATENT NO. : 5,705,698
DATED : January 6, 1998
INVENTOR(S) : Lowell J. Lawrence et al.

It is certified that error appears in the above-identified patent and that said Letters Patent is hereby corrected as shown below:

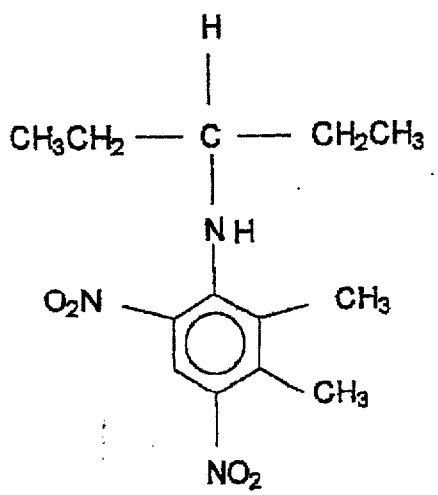

In Column 3, line 17, following "dialkylanilines", add --including--.
In Column 3, line 18, change "selected" to --selective--.
In Column 3, line 64, change "isometrically" to --isomerically--.
In Column 4, lines 2-3, delete "aromatic".
In Column 4, lines 15, 17 and 21, delete "desired".
In Column 4, line 16, change "2" to --I--.

UNITED STATES PATENT AND TRADEMARK OFFICE
CERTIFICATE OF CORRECTION

PATENT NO. : 5,705,698
DATED : January 6, 1998
INVENTOR(S) : Lowell J. Lawrence et al.

It is certified that error appears in the above-identified patent and that said Letters Patent is hereby corrected as shown below:

In Column 4, line 18, following "intermediate", insert --[I]--.
In Column 4, line 21, following "intermediate", insert --[II]--.
In Column 4, line 30, change "other undesired" to --residual--.
In Column 4, lines 33-35, delete "Next is...Specifically," and insert --To obtain pure pendimethalin--.
In Column 4, line 36, following "diate", insert --[I]--.
In Column 4, line 42, delete "Next is the amination step." (no new paragraph).
In Column 4, lines 51-52, delete "By following ... pendimethalin".
In Column 4, line 55, delete "previously "undesired"".
In Column 4, line 56, change "compounds" to --compound [II]--.
In Column 5, lines 1 and 3, delete ""undesired"".
In Column 5, line 24, change "O-xylene" to --o-xylene-- and insert --3,4,5--- prior to "Trinitro-o-".
In Column 5, line 25, after "Derivative", insert --[I]--.
In Column 5, line 51, delete "desired".
In Column 5, lines 51, 57 and 66, change

UNITED STATES PATENT AND TRADEMARK OFFICE
CERTIFICATE OF CORRECTION

PATENT NO. : 5,705,698

DATED : January 6, 1998

INVENTOR(S) : Lowell J. Lawrence et al

It is certified that error appears in the above-identified patent and that said Letters Patent is hereby corrected as shown below:

"1,2,6" to --3,4,5--.

In Column 5, lines 62-63, change "3,4-dimethyl-2,6-dinitro-N-(ethylpropyl) aniline, Pendimethalin" to --N-(1-ethylpropyl)-3,4-dimethyl-2,6 dinitroaniline [III]--.

In Column 6, line 22, change "1,4,6-Trinitro-O-xylene" to --3,4,6-Trinitro-o-xylene [II]--.

In Column 6, line 30, change "1,4,6-trinitro-o-xylene" to --3,4,6-trinitro-o-xylene [II]--.

In Column 6, lines 35-36, change "2,3-dimethyl-4,6-dinitro-N-(1-ethylpropyl) aniline, Iso-pendimethalin" to --N-(1-ethylpropyl)-2,3-dimethyl-4,6-dinitroaniline [IV]--.

In Column 6, line 37, change "1,4,6" to --3,4,6--.

In Column 6, line 39, change "of" to --that the-- and delete "that" following "time".

In Column 7, line 3, change "ration" to --molar ratio--.

UNITED STATES PATENT AND TRADEMARK OFFICE
CERTIFICATE OF CORRECTION

PATENT NO. : 5,705,698
DATED : January 6, 1998
INVENTOR(S) : Lowell J. Lawrence et al.

It is certified that error appears in the above-identified patent and that said Letters Patent is hereby corrected as shown below:

In Column 7, line 13, change "heating" to --stirring--.
In Column 7, lines 27, 28 and 41, change "isometrically" to --isomerically--.
In Column 8, line 19, change "isometrically" to --isomerically--.

Signed and Sealed this

Twenty-fifth Day of August, 1998

Attest:

BRUCE LEHMAN

Attesting Officer  Commissioner of Patents and Trademarks